United States Patent [19]

Ruske et al.

[11] Patent Number: 5,424,404
[45] Date of Patent: Jun. 13, 1995

[54] BISCATIONIC AZO DYES AND INTERMEDIATES THEREFOR

[75] Inventors: Manfred Ruske, Ludwigshafen; Udo Mayer, Frankenthal, both of Germany

[73] Assignee: BASF Aktiengesellschaft, Ludwigshafen, Germany

[21] Appl. No.: 75,019

[22] Filed: Jun. 11, 1993

Related U.S. Application Data

[63] Continuation of Ser. No. 762,387, Sep. 19, 1991, abandoned.

[30] Foreign Application Priority Data

Oct. 26, 1990 [DE] Germany .......... 40 34 060.0

[51] Int. Cl.$^6$ .......... C09B 35/031; C09B 44/08; C09B 57/00; D06P 1/41
[52] U.S. Cl. .......... 534/606; 534/607; 534/608; 546/187; 546/256
[58] Field of Search .......... 534/606, 607, 608; 546/187, 256

[56] References Cited

U.S. PATENT DOCUMENTS

| | | | |
|---|---|---|---|
| 4,213,897 | 7/1980 | Moser et al. | 534/606 |
| 4,483,796 | 11/1984 | Doswald et al. | 534/604 |
| 4,675,388 | 6/1987 | Greve et al. | 534/608 |
| 4,742,161 | 5/1988 | Dore | 534/606 |
| 5,001,226 | 3/1991 | Moser et al. | 534/606 |
| 5,015,292 | 5/1991 | Bruder et al. | 106/22 |
| 5,023,324 | 6/1991 | Moser | 534/606 |
| 5,037,964 | 8/1991 | Moser et al. | 534/608 |
| 5,059,683 | 10/1991 | Moser et al. | 534/759 |
| 5,077,396 | 12/1991 | Moser et al. | 534/606 |

FOREIGN PATENT DOCUMENTS

| | | | |
|---|---|---|---|
| 2920487 | 11/1979 | Germany | 534/606 |
| 3538517 | 5/1986 | Germany | 534/606 |
| 2173210 | 10/1986 | United Kingdom | 534/606 |

*Primary Examiner*—Floyd D. Higel
*Attorney, Agent, or Firm*—Oblon, Spivak, McClelland, Maier & Neustadt

[57] ABSTRACT

Biscationic azo dyes useful for dyeing or printing polymeric material have the formula

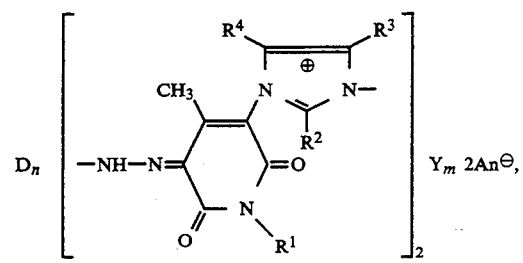

where
$R^1$ is hydrogen or unsubstituted or phenyl-substituted $C_1$–$C_5$-alkyl,
$R^2$ is hydrogen or $C_1$–$C_5$-alkyl,
$R^3$ and $R^4$ are independently of each other hydrogen or methyl,
D is the radical of a diazo component, unsubstituted or substituted phenylene or a radical of the formula

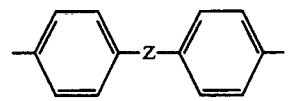

where
Z is a bridge member, Y is hydrogen, $C_1$–$C_{18}$-alkyl, $C_2$–$C_6$-alkylene, xylidene or phenylene,
$An^\ominus$ is one equivalent of an anion,
m is 1 or 2, and
n is 1 or 2,

5 Claims, No Drawings

BISCATIONIC AZO DYES AND INTERMEDIATES THEREFOR

This application is a Continuation of application Ser. No. 07/762,387, filed on Sep. 19, 1991, now abandoned.

The present invention relates to novel bis cationic azo dyes of the formula I

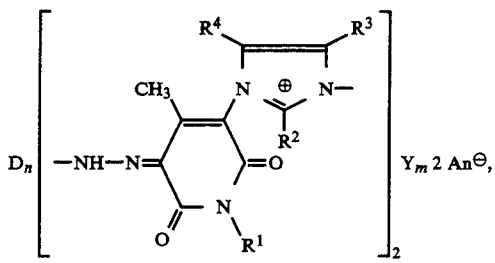

where
R$^1$ is hydrogen or unsubstituted or phenyl-substituted C$_1$–C$_5$-alkyl,
R$^2$ is hydrogen or C$_1$–C$_5$-alkyl,
R$^3$ and R$^4$ are identical or different and each is independently of the other hydrogen or methyl,
D is the radical of a sulfo-devoid aromatic diazo component, unsubstituted or C$_1$–C$_4$-alkyl- or C$_1$–C$_4$-alkoxy-substituted 1,4-phenylene or a radical of the formula

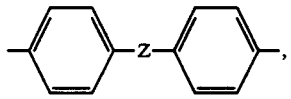

where
Z is a bridge member,
Y is hydrogen, C$_1$–C$_{18}$-alkyl, C$_2$–C$_6$-alkylene, xylidene or phenylene,
An$^\ominus$ is one equivalent of an anion,
m is 1 or 2, and
n is 1 or 2,
with the proviso that
a) in the case of Y being hydrogen or C$_1$–C$_{18}$-alkyl, m is 2, n is 1 and D is unsubstituted or C$_1$–C$_4$-alkyl or C$_1$–C$_4$-alkoxy-substituted 1,4-phenylene or a radical of the formula

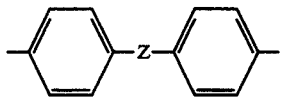

and
b) in the case of Y being C$_2$–C$_6$-alkylene, xylidene or phenylene, m is 1, n is 2 and D is the radical of a sulfo-devoid aromatic diazo component,
to intermediates therefor and to the use of the novel dyes for dyeing or printing polymeric material.

Cationic azo dyes are already known from, DE-A-2 054 697, DE-A-2 627 680, DE-A-3 538 517 and EP-A-92 520.

It is an object of the present invention to provide novel biscationic azo dyes which have advantageous application properties.

We have found that this object is achieved by the biscationic azo dyes of the formula I defined at the beginning.

The biscationic azo dyes of the formula I can exist in various tautomeric forms, which are all encompassed by the claim.

Any alkyl or alkylene appearing in the above-mentioned formula I may be either straight-chain or branched.

R$^1$, R$^2$ and Y are each for example methyl, ethyl, propyl, isopropyl, butyl, isobutyl, sec-butyl, tert-butyl, pentyl, isopentyl, neopentyl or tert-pentyl.

R$^1$ may also be for example benzyl or 1- or 2-phenylethyl.

Y may also be for example hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl (the foregoing terms isooctyl, isononyl, isodecyl and isotridecyl are trivial names derived from oxo process alcohols - cf. Ullmanns Encyklopädie der technischen Chemie,4th volume 7 pages 215 to 217, and volume 11, pages 435 and 436), methylene, ethylene, 1,2-or 1,3propylene, 1,2-, 1,3-, 1,4-, or 2,3-butylene, 1,5-pentylene or 1,6-hexylene.

When d is the radical of sulfo-devoid aromatic diazo component, the free amines of the formula D—NH$_2$ are aminoanthraquinone, aminothiazole, aminobenzothiazole or aminotriazole series.

These amines D—NH$_2$ may be monosubstituted or polysubstituted, generally mono-, di- or trisubstituted, suitable substituents being for example halogen, such as chlorine or bromine, nitro, C$_1$–C$_4$-alkoxy, benzloxy, phenoxy, halophenoxy, C$_1$–C$_4$-alkyl, phenyl, trifluoromethyl, carbamoylmethyl, N-phenylcarbamoylmethyl, C$_1$–C$_4$-alkanoyl, benzoyl, mono- or di-C$_1$–C$_4$-alklbenzoyl, mono- or di-C$_1$–C$_4$alkoxybenzoyl, (C$_1$–C$_4$-alkyl) (C$_1$–C$_4$-alkoxy)benzoyl, dimethylaminoacetyl, C$_1$–C$_4$-alkoxycarbonyl, carbamoyl, C$_1$–C$_4$-mono- or -dialkylcarbamoyl, cyano, C$_1$–C$_4$-alkanoylamino, benzoylamino, phthalimido, phenylamino, mono- or dinitrophenylamino, C$_1$–C$_4$-alkylsulfonyl, phenoxysulfonyl, sulfamoyl, C$_1$–C$_4$-mono- or dialkylsulfamoyl, phenylsulfamoyl, N-(C$_1$–C$_4$-alkyl)-N-phenylsulfamoyl, halophenylsulfamoyl, naphthylsulfamoyl, phenylazo, nitrophenylazo, C$_1$–C$_4$alkanoylaminophenylazo or C$_1$–C$_4$dialkylaminophenylazo.

The following amines may be mentioned by way of example: aniline, 1-amino-2-chlorobenzene, 1-amino-3-chlorobenzene, 1-amino-2,6-dichlorobenzene, 1-amino-2,3-dichlorobenzene, 1-amino-2,5-dichlorobenzene, 1-amino-2,4-dichlorobenzene, 1-amino-3,4-dichlorobenzene, 1-amino-3,5-dichlorobenzene, 1-amino-4-acetaminobenzene, 1-amino-2-chloro-4-acetaminobenzene, 1-amino-4-benzoylaminobenzene, 1-amino-4-phenylbenzene, 4-amino-1,1'-diphenyl ether, 4-amino-4'-chloro-1,1'-diphenyl ether, 2-amino-4'-chloro-1,1'-diphenyl ether, 2-amino-1,1'-diphenyl ether, 1-amino-2-chloro-4-methylsulfonylbenzene, 1-amino-4-methylsulfonylbenzene, phenyl 1-aminobenzene-3-sulfonate, phenyl 1-aminobenzene-4-sulfonate, phenyl 1-amino-2-chlorobenzene-5-sulfonate, phenyl 1-amino-2-methylbenzene-5-sulfonate, phenyl 1-amino-2,6-dichlorobenzene-4-sulfonate, 1-amino-3-trifluoromethylbenzene, 1-amino-3,5-bis(trifluoromethyl)benzene, 1-amino-2-trifluoromethyl-4-chlorobenzene, 1-amino-4-ethoxycarbonylaminobenzene, 1-amino-2,5-dimethoxy-4-ethoxycarbonylaminobenzene, 1-aminonaphthalene, 1- aminonaphthalene-4-sulfondimethylamide, 4-aminophenylphthalimide, dimethyl 2-aminoterephthalate, 4-aminobenzophenone, 4-amino-4′-methylbenzophenone, 1-amino-4-acetylbenzene, 4-amino-2′,4′-dinitrodiphenylamine, 4-amino-4′-nitrodiphenylamine, 4-amino-2′-nitrodiphenylamine, 1-amino-2-methylbenzene, 1-amino-3-methylbenzene, 1-amino-4-methylbenzene, 1-amino-2,5-dimethylbenzene, 1-amino-2-methyl-3-chlorobenzene, 1-amino-2-methyl-6-chlorobenzene, 1-amino-2-methyl-5-chlorobenzene, 1-amino-2-chloro-4-methylbenzene, 1-amino-3-chloro-4-methylbenzene, 1-amino-3,6-dichloro-4-methylsulfamoylbenzene, 1-amino-2-chloro-4-nitrobenzene, 1-amino-2-bromo-4-nitrobenzene, 1-amino-2,5-dichloro-4-methoxybenzene, 1-amino-2-methoxybenzene, 1-amino-4-methoxybenzene, 1-amino-2,5-dimethylbenzene, 1-amino-2-methyl-3-chlorobenzene, 1-amino-2-methyl-6-chlorobenzene, 1-amino-2-methyl-5-chlorobenzene, 1-amino-2-chloro-4-methylbenzene, 1-amino-3-chloro-4-methylbenzene, 1-amino-3,6-dichloro-4-dimethylsulfamoylbenzene, 1-amino-2-chloro-4-nitrobenzene, 1-amino-2-bromo-4-nitrobenzene, 1-amino-2,5-dichloro-4-methoxybenzene, 1-amino-2-methoxybenzene, 1-amino-4-methoxybenzene, 1-amino-3-chloro-4-methoxybenzene, 1-amino-2-ethoxybenzene, 1-amino-4-ethoxybenzene, 1-amino-4-benzyloxybenzene, 1-amino-phenylacetamide. 1-aminophenylacetanilide, 1-amino-2-cyanobenzene, 1-amino-4-cyanobenzene, 1-amino-3-cyanobenzene, 1-amino-2-cyano-4-nitrobenzene, 1-amino-2-cyano-4-nitro-6-bromobenzene, 1-amino-2-nitro-4-methylbenzene, 1-amino-2-nitro-4-chlorobenzene, 1-amino-2,5-dimethoxy-4-chlorobenzene, 1-amino-2,5-dimethoxy-4-bromobenzene, 1-amino-2,5-dimethoxybenzene, 1-amino-2,5-diethoxybenzene, 1-amino-2,5-dimethoxy-4-acetaminobenzene, 1-amino-2,5-dimethoxy-4-benzoylaminobenzene, 1-amino-2,5-diethoxy-4-benzoylaminobenzene, 1-aminobenzene-4-(N-methyl)sulfonamide, 1-aminobenzene-4-(N,N-dimethyl)sulfonamide, 1-aminobenzene-4-(N-phenyl)sulfonamide, 1-aminobenzene-4-(N-2′-chlorophenyl)sulfonamide, 1-aminobenzene-3-(N-phenyl)sulfonamide, 1-aminobenzene-2-(N-ethyl-N-phenyl)sulfonamide, 1-amino-2-methyl-5-sulfamoylbenzene, 1-amino-4-methylbenzene-3-(N-ethyl-N-phenyl)sulfonamide, 1-amino-4-methylbenzene-3-(N-phenyl)sulfonamide, 1-amino-2,5-dichlorobenzene-4-(N-phenyl)sulfonamide, 1-amino-3-nitrobenzene, 1-amino-4-nitrobenzene, 1-amino-2-methoxy-4-nitrobenzene, 1-amino-2,5-dimethoxy-4-nitrobenzene, 1-amino-2,5-dinitrobenzene, methyl 1-aminobenzene-4-carboxylate, ethyl 1-aminobenzene-4-carboxylate, ethyl 1-amino-2-methylbenzene-4-carboxylate, 1-amino-2-methylbenzene-4-(N-phenyl)carboxamide, 1-aminobenzene-4-(N-phenyl)carboxamide, 1-aminobenzene-4-(N,N-dimethyl)carboxamide, 2-aminobenzamide, methyl 1-amino-4-chlorobenzene-2-carboxylate, methyl 1-aminobenzene-2-carboxylate, methyl 1-aminobenzene-3-carboxylate, 1-aminobenzene-3-(N-phenyl)carboxamide, 1-amino-3-nitro-4-methylbenzene, 1-amino-2-nitro-4-methoxybenzene, 1-amino-3-acetaminobenzene, 1-amino-benzene-4-(N-1-naphthyl)-sulfonamide, 1-amino-3-acetaminobenzene, 1-amino-2-nitro-4-methylbenzene, 1-amino-2,4,6-trichlorobenzene, 1-amino-4-(dimethylaminoacetyl)benzene, 1-amino-2-nitro-4-acetaminobenzene, 4-aminoazobenzene, 4-amino-2-methyl-5-methoxyazobenzene, 4-amino-2,5-dimethoxyazobenzene, 4-amino-4′-nitroazobenzene, 4-amino-4′-acetaminoazobenzene, 4-amino-4′-dimethylaminoazobenzene, 1-amino-4′-phenylazonaphthalene, 1-amino-2-ethoxy-4′-phenylazonaphthalene, 4-amino-3′-methylazobenzene, 4-amino-4′-methylazobenzene, 2-aminoanthraquinone, 2-aminothiazole, 2-amino-5-methoxybenzothiazole, 2-aminobenzothiazole-6-sulfonamide and 3-amino-1,2,4-triazole.

When D is a radical of the formula

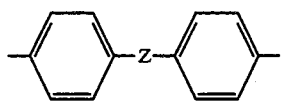

suitable bridge members Z are for example $C_2$–$C_6$alkylene, $C_2$–$C_6$alkylenoxy or a radical of the formula —CH=CH—, —NH—CO—, —N=N—, —NH—CO—NH—,

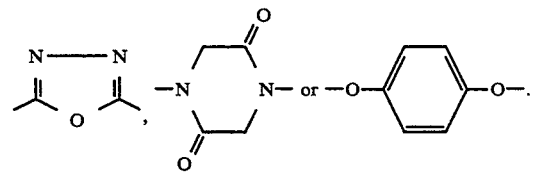

Suitable anions $An^\ominus$ are for example fluoride, chloride, bromide, iodide, formate, acetate, propionate, mono-, di- or trichloroacetate, hydroxyacetate, methoxyacetate, 2-hydroxyethoxyacetate, lactate, citrate, succinate, glutarate, methanesulfonate, benzenesulfonate and 2- or 4methylbenzensulfonate.

When D is the radical of a sulfo-devoid aromatic diazo component, preference is given to those biscationic azo dyes of the formula I where D is the radical of a diazo component of the aniline series.

Of special importance are biscationic azo dyes of the formula I where

Y is hydrogen or $C_1$–$C_5$-alkyl,

D is phenylene or a radical of the formula

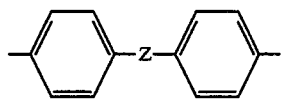

where

Z is a defined above, m is 2, and n is 1.

Also of special importance are biscationic azo dyes of the formula I where

Y is $C_2$–$C_6$-alkylene, xylidene or phenylene,

D is the radical of a sulfo-devoid diazo component of the aniline series, m is 1, and n is 2.

The present invention further provides doubled imidazolypyridones of the formula II

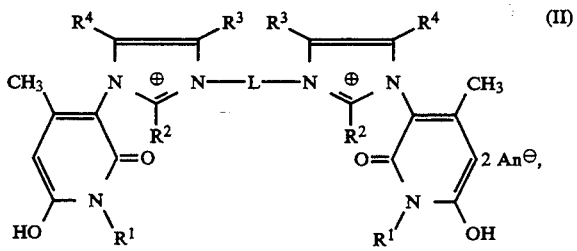

where
L is $C_2$-$C_6$-alkylene, xylidene or phenylene,
$R^1$ is hydrogen or unsubstituted or phenyl-substituted $C_1$-$C_5$-alkyl,
$R^2$ is hydrogen or $C_1$-$C_5$-alkyl,
$R^3$ and $R^4$ are identical or different and each is independently of the other hydrogen or methyl, and
$An^\ominus$ is one equivalent of an anion.

For examples of the radicals appearing in the formula II, reference should be made to the earlier lists.

The novel biscationic dyes of the formula I may be prepared in a conventional manner, for example by diazotizing an amine of the formula IIIa $$D^1—NH_2 \qquad (IIIa),$$

where $D^1$ is the radical of a sulfo-devoid aromatic diazo component, and coupling to a doubled imidazolylpyridone of the formula II.

It is also possible to tetrazotize a diamine of the formula IIIb $$H_2N—D^2—NH_2 \qquad (IIIb),$$

where $D^2$ is unsubstituted or $C_1$-$C_4$-alkyl- or $C_1$-$C_4$-alkoxy-substituted 1,4-phenylene or a radical of the formula

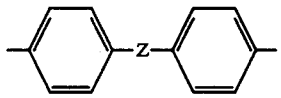

where Z is as defined above, and couple the diazonium salt to an imidazolylpyridone of the formula IV

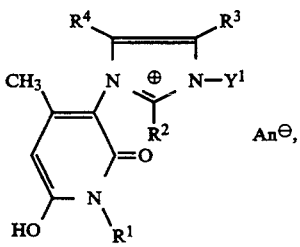

where $R^1$, $R^2$, $R^3$, $R^4$ and $An^\ominus$ are each as defined above and $Y^1$ is hydrogen or $C_1$-$C_8$-alkyl.

The diazotization of amines of the formula IIIa and the tetrazotization of diamines of the formula IIIb, like the coupling to the coupling components of the formulae II and IV, can be carried out by known methods.

Advantageously the couplings are effected in an aqueous, acidic or neutral to weakly alkaline medium in the presence of buffers, such as the alkali metal salts of formic, acetic or propionic acid, the alkali metal salts of dicarboxylic acids, such as succinic, glutaric or adipic acid, the alkali metal salts of phosphoric acid or carbonic acid or mixtures thereof.

The dye is advantageously isolated as a dyebase at above pH 9. However, it is also possible to use the reaction solution directly.

For use the dyebases are advantageously converted into the readily water-soluble 4-methyl-6-hydroxpyrid-2-one-3-imidazolium salts by dissolving in dilute aqueous acids, such as formic acid, acetic acid, propionic acid, lactic acid, citric acid, glycolic acid, diglycolic acid, succinic acid, glutaric acid, methanesulfonic acid, sulfamic acid or mixtures thereof, and thus converted into a stable liquid form.

To increase the flowability and lengthen the shelf life it is possible to add glycols, such as diethylene glycol or triethylene glycol, glycol ethers, urea, formamide or N-methylpyrrolidinone.

The imidazolylpyridones of the formula IV are likewise obtained by known methods, for example by condensing an imidazolylacetamide hydrochloride with methyl acetoacetate in an alcoholic sodium methoxide solution.

The imidazolylpyridones of the formula IV can be used to prepare the doubled imidazolylpyridones of the formula II, for example by reaction with a compound of the formula V $$X—L—X \qquad (V),$$

where L is as defined above and X is a leaving group (e.g. chlorine, bromine, iodine, methosulfate, ethosulfate, benzenesulfonate or toluenesulfonate).

Preferably, however, the imidazolylpyridones of the formula II are prepared by condensing diimidazoles of the formula VI

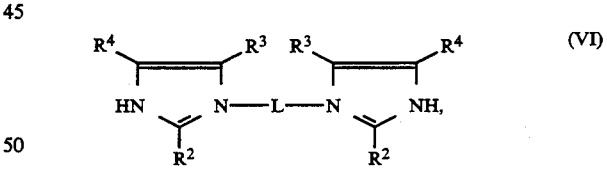

where L, $R^2$, $R^3$ and $R^4$ are each as defined above, with chloroacetamide or N- ($C_1$-$C_5$-alkyl) chloroacetamides to give compounds of the formula VII

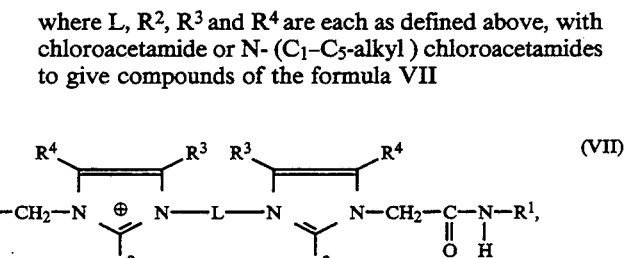

where L, $R^1$, $R^2$, $R^3$, $R^4$ and $An^\ominus$ are each as defined above. These compounds can then be converted in a Knoevenagel reaction in the presence of basic catalysts into the imidazolylpyridones of the formula II.

The preparation of the diimidazoles VI is described for example in DE-A-2 903 653, J. prakt. Chem. 280 (1959), 306–313, or Chem. Heterocycl. Comp. 6 (1970), 194–197.

The novel biscationic azo dyes of the formula I can be employed alone or mixed with one another or with other cationic or anionic compounds in the form of solutions or in the form of powders or granules.

They are advantageously useful for dyeing or printing polymeric material, in particular paper stock, but also cellulose, cotton, leather, bast fiber, hemp, flax, sisal, jute, coir or straw.

The dyes are preferably used in the making of wet end colored, sized or unsized paper. They can likewise be used for coloring paper by the dip method.

The dyeing of paper, leather or cellulose takes place in a conventional manner.

The novel dyes, or preparations thereof, leave virtually no if any residues in the wastewater from papermaking, a particularly favorable aspect from the viewpoint of minimizing water pollution. They are highly substantive, do not mottle when applied to paper, and are substantially pH-insensitive. The dyeings on paper are noteworthy for good lightfastness. Following prolonged exposure to light, the shade changes on-tone.

The colored papers are wet-fast, not only to water but also to milk, soapy water, sodium chloride solutions, fruit juices or sugared mineral water and, on account of their good alcohol fastness, they are also resistant to alcoholic beverages.

The novel dyes can also be used for dyeing, padding or printing acrylic textiles or anionically modified polyamide or polyester textiles.

The Examples which follow will further illustrate the invention. The percentages are in each case by weight.

EXAMPLE 1

5.3 g of 4,4'-diaminodibenzyl, 35 ml of water and 20.4 g of 30% strength hydrochloric acid were admixed with 100 g of ice and tetrazotized in a conventional manner at 0°–5° C. with 3.5 g of sodium nitrite, dissolved in water. After the excess nitrite had been removed with sulfamic acid, the cold solution of the tetrazonium chloride was added to 200 g of 10% strength sodium acetate solution and a little ice at the same time as a solution of 13.5 g of 3-(3-propylimidazolium)-4-methyl-6-hydroxypyrid-2-one chloride in 175 ml of water and 2 g of acetic acid. The reaction mixture was stirred at pH 4–5 and 20°–22° C. for one hour until coupling was complete. The reaction mixture was then brought with 10% strength sodium carbonate solution to pH 9.5 and briefly heated to 80° C.

The readily formed precipitate of the dyebase of the formula

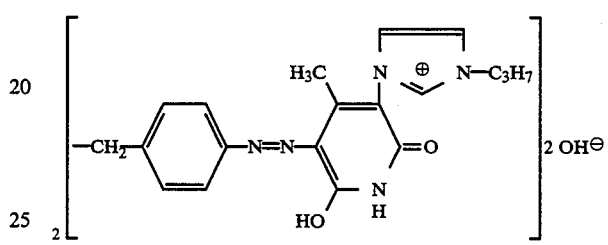

was filtered off, washed with water and dried, giving 17.7 g of dyebase. The solution of the dyebase as acetate in aqueous acetic acid had an absorption maximum ($\lambda_{max}$) of 442.1 nm. In tissue wet end coloring the dye showed high affinity even under neutral conditions. The bleed fastness of the yellow dyeings on paper in distilled water, 1.5% strength acetic acid, 0.5% strength sodium carbonate solution and 50% strength ethanol was very good in each test medium.

The method of Example 1 can also be used to obtain the dyes listed in Table 1.

TABLE 1

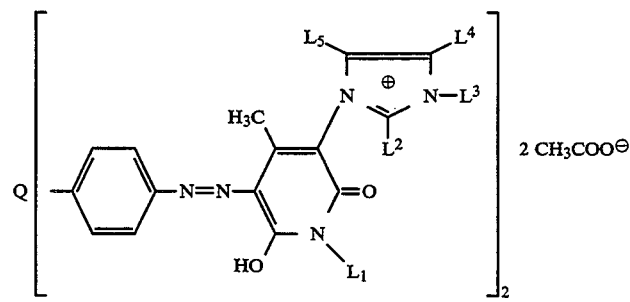

| Example No. | Q | $L_1$ | $L^2$ | $L^3$ | $L^4$ | $L_5$ | $\lambda_{max}$ [nm] |
|---|---|---|---|---|---|---|---|
| 2 | —CH$_2$—CH$_2$— | CH$_3$ | H | CH$_3$ | H | H | 441.1 |
| 3 | —CH$_2$—CH$_2$— | H | H | CH$_3$ | H | H | 441.1 |
| 4 | —CH$_2$—CH$_2$— | H | H | i-propyl | H | H | 441.1 |
| 5 | —CH$_2$—CH$_2$— | H | CH$_3$ | CH$_3$ | H | H | 442.1 |
| 6 | —CH$_2$—CH$_2$— | H | H | CH$_3$ | H | CH$_3$ | 442.1 |
| 7 | —CH$_2$—CH$_2$— | H | H | CH$_3$ | CH$_3$ | H | 441.1 |
| 8 | —NH—CO— | CH$_3$ | H | CH$_3$ | H | H | 456.1 |
| 9 | —NH—CO— | CH$_3$ | H | C$_2$H$_5$ | H | H | 448.1 |
| 10 | —NH—CO— | CH$_3$ | H | C$_3$H$_7$ | H | H | 457.1 |
| 11 | —NH—CO— | CH$_3$ | H | CH$_3$ | H | CH$_3$ | 453.1 |
| 12 | —NH—CO— | CH$_3$ | H | i-propyl | H | H | 457.1 |
| 13 | —NH—CO— | H | H | CH$_3$ | H | H | 454.1 |
| 14 | —NH—CO— | H | H | C$_2$H$_5$ | H | H | 448.1 |
| 15 | —NH—CO— | H | H | C$_3$H$_7$ | H | H | 457.1 |
| 16 | —NH—CO— | H | H | i-propyl | H | H | 453.1 |
| 17 | —NH—CO— | H | CH$_3$ | CH$_3$ | H | H | 458.1 |
| 18 | —NH—CO— | H | H | CH$_3$ | H | CH$_3$ | 456.1 |
| 19 | —N=N— | H | CH$_3$ | CH$_3$ | H | H | 500.1 |

TABLE 1-continued

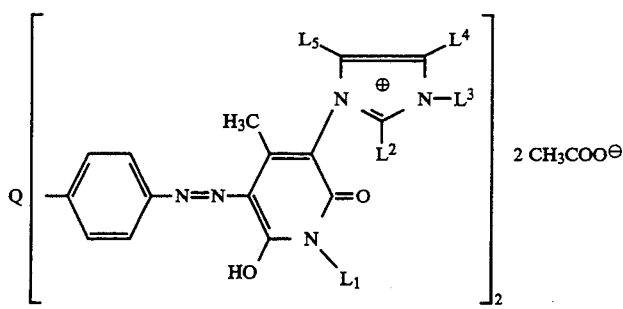

| Example No. | Q | $L_1$ | $L^2$ | $L^3$ | $L^4$ | $L_5$ | $\lambda_{max}$ [nm] |
|---|---|---|---|---|---|---|---|
| 20 | —O(CH$_2$)$_3$— | H | CH$_3$ | CH$_3$ | H | H | 447.1 |
| 21 | —NH—CO—NH— | H | H | CH$_3$ | H | H | 478.1 |
| 22 | —NH—CO—NH— | H | H | C$_2$H$_5$ | H | H | 476 |
| 23 | —NH—CO—NH— | H | H | C$_3$H$_7$ | H | H | 481.1 |
| 24 | —NH—CO—NH— | H | H | i-propyl | H | H | 478.1 |
| 25 | —NH—CO—NH— | H | CH$_3$ | CH$_3$ | H | H | 480.1 |
| 26 | —NH—CO—NH— | H | H | CH$_3$ | H | CH$_3$ | 479 |
| 27 | —NH—CO—NH— | CH$_3$ | H | CH$_3$ | H | H | 476.1 |
| 28 | —NH—CO—NH— | CH$_3$ | H | C$_2$H$_5$ | H | H | 476.1 |
| 29 | —NH—CO—NH— | CH$_3$ | H | C$_3$H$_7$ | H | H | 481.1 |
| 30 | —NH—CO—NH— | CH$_3$ | H | i-propyl | H | H | 480.1 |
| 31 | —NH—CO—NH— | CH$_3$ | H | H | H | CH$_3$ | 478.1 |
| 32 | —N=N— | H | H | CH$_3$ | H | H | 495 |

EXAMPLE 33

14.25 g of 3-(3-methylimidazolium)-4-methyl-5-[azo-(4-aminophenyl)]-1-methylpyrid-2,6-dione chloride (prepared by hydrochloric acid hydrolysis of the 4'-acetylaminobenzene) were dissolved in 50 ml of water and 20 g of 30% strength acetic acid and, after ice had been added, diazotized in a conventional manner at 0°–5° C. with 2.8 g of sodium nitrite. The diazonium chloride was reacted with a solution of 10.26 g of 2-(3-methylimidazolium)-1,4-dimethylpyrid-2,6-dione chloride in 120 ml of water and 2 g of 30% strength acetic acid in the presence of 30 g of 10 % strength sodium acetate solution at pH 4–5 and 5°–15° C.

The dyebase was precipitated at pH 9.5 with sodium carbonate solution, heated to 60° C., filtered off, washed salt-free with water and dried. This gave 10.3 g of a red dye of the formula

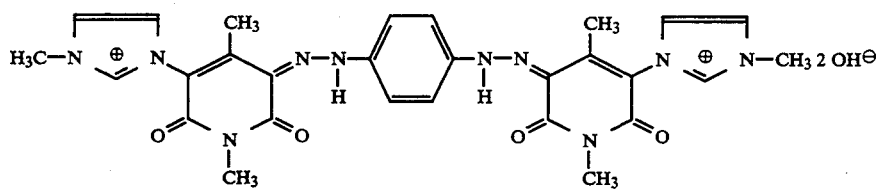

$\lambda_{max}$ (acetic acid): 513.1 nm.

Paper was dyed a very deep bluish red at pH 4–5.

The method of Example 33 can also be used to obtain the dyes of the formula

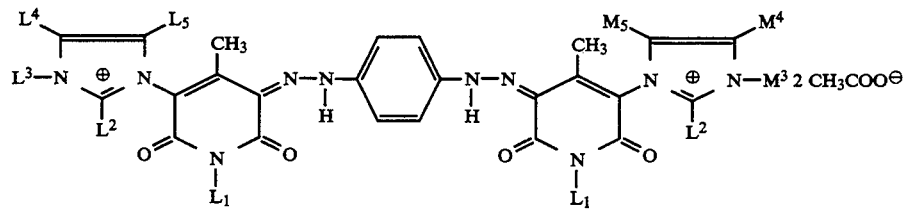

listed below in Table 2.

TABLE 2

| Example No. | $L_1$ | $L^2$ | $L^3$ | $L^4$ | $L_5$ | $M^1$ | $M^2$ | $M^3$ | $M^4$ | $M_5$ | $\lambda_{max}$ [nm] |
|---|---|---|---|---|---|---|---|---|---|---|---|
| 34 | H | H | C$_3$H$_7$ | H | H | H | H | C$_3$H$_7$ | H | H | 514.1 |
| 35 | H | H | C$_3$H$_7$ | H | H | CH$_3$ | H | CH$_3$ | H | H | 514.1 |
| 36 | CH$_3$ | H | CH$_3$ | H | H | CH$_3$ | H | CH$_3$ | H | H | 513.1 |
| 37 | H | H | CH$_3$ | H | H | CH$_3$ | H | CH$_3$ | H | H | 514.1 |
| 38 | H | H | CH$_3$ | H | H | H | H | CH$_3$ | H | H | 514.1 |
| 39 | H | H | CH$_3$ | H | H | H | H | C$_3$H$_7$ | H | H | 515.1 |

EXAMPLE 40

7.5 g of 1-amino-4-acetylaminobenzene were finely suspended in 45 g of ice-water and admixed at 0°–5° C. with 25 g of 18% strength hydrochloric acid. After further ice had been added, 3.45 g of sodium nitrite were added in aqueous solution. After about 30 minutes the diazonium chloride formed was added to a very finely divided suspension of 12 g of 1,2-bis(4-methyl-6-hydroxypyrid-2-on-3-imidazolium)ethane chloride in 150 ml of water and 6.5 g of acetic acid. After the coupling had ended, the mixture was adjusted to pH 9 and heated at 80° C. The suspension was filtered at 25° C., and the filter residue was washed salt-free with water. This left 16.8 g of a dyebase of the formula

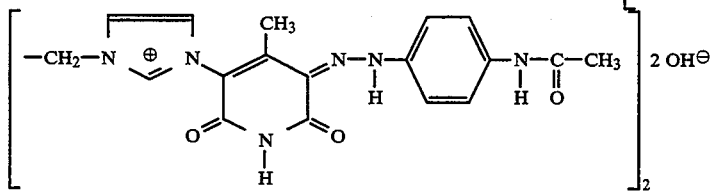

λ_{max} acetic acid): 448.1 nm.

EXAMPLE 41

Example 40 was repeated, except that the 1-amino-4-acetylaminobenzene was replaced by 3.2 g of 1-amino-4-benzoylaminobenzene, affording 21.3 g of a yellow dye of the formula

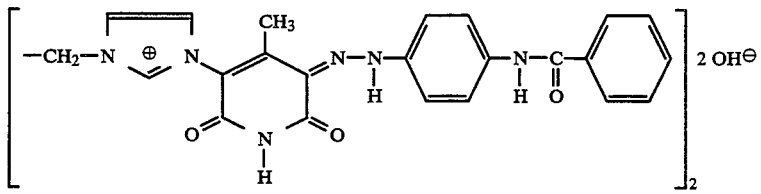

λ_{max} (acetic acid): 447.1 nm. The dye has very high affinity for paper.

EXAMPLE 42

Example 40 was repeated, except that the 1-amino-4-acetylaminobenzene was replaced by 6.1 g of p-anisidine, affording 11.2 g of a yellow dyebase of the formula

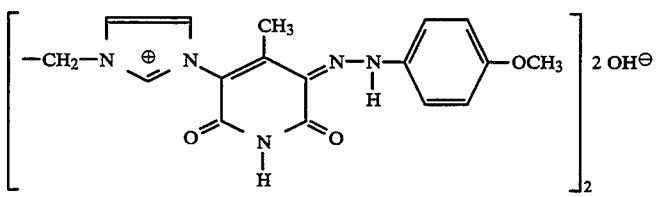

λ_{max} (acetic acid): 455.1.

Diazotizing aromatic amines of the formula Q—NH₂ in a conventional manner and coupling to a 1,2-bis-(4-methyl-6-hydroxypyrid-2-on-imidazolium)ethane chloride gave dyebases of the formula

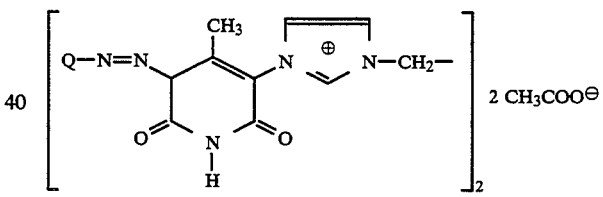

which, measured in 10% strength acetic acid, have the absorbance values indicated in Table 3.

TABLE 3

| Example No. | Q | λ_{max} [nm] |
|---|---|---|
| 43 | 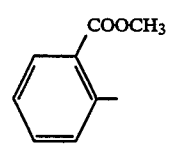 | 420 |
| 44 | COOCH₃ (ortho-substituted phenyl) | 422 |

TABLE 3-continued

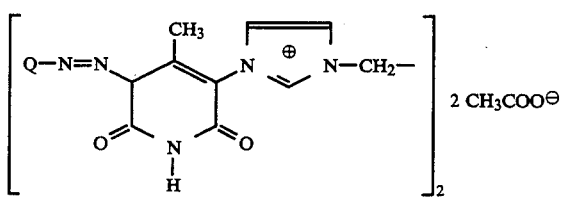
2 CH₃COO⁻

| Example No. | Q | λ$_{max}$ [nm] |
|---|---|---|
| 45 | 4-acetylphenyl (H₃C-CO-C₆H₄-) | 425 |
| 46 | 2-carbamoylphenyl (2-CONH₂-C₆H₄-) | 425 |
| 47 | phenyl | 426 |
| 48 | 3-methoxyphenyl | 429 |
| 49 | 4-methylphenyl | 436.1 |
| 50 | 4-ethoxyphenyl | 451 |
| 51 | 2-methoxyphenyl | 451 |
| 52 | 2-ethoxyphenyl | 451 |
| 53 | 4-phenoxyphenyl | 442 |
| 54 | 2,4-dimethylphenyl | 444 |

TABLE 3-continued

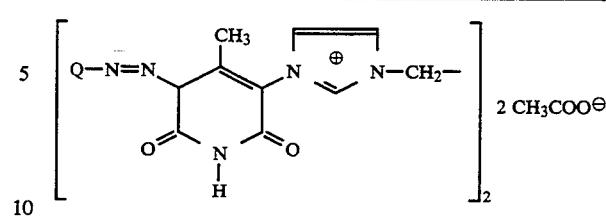
2 CH₃COO⁻

| Example No. | Q | λ$_{max}$ [nm] |
|---|---|---|
| 55 | 2,4-dimethyl-5-methoxyphenyl | 460 |
| 56 | 4-methoxy-(4-acetamido)phenyl | 462 |
| 57 | 2,5-dimethyl-benzoylphenyl | 426.1 |
| 58 | 4-methoxy-benzoylphenyl | 426.1 |
| 59 | 4-isopropyl-benzoylphenyl | 425.1 |
| 60 | 2-methoxy-5-methyl-benzoylphenyl | 427.1 |
| 61 | 4-ethoxy-benzoylphenyl | 426.1 |
| 62 | 4-ethyl-benzoylphenyl | 425.1 |
| 63 | 2-methyl-4-ethyl-benzoylphenyl | 427.1 |

TABLE 3-continued

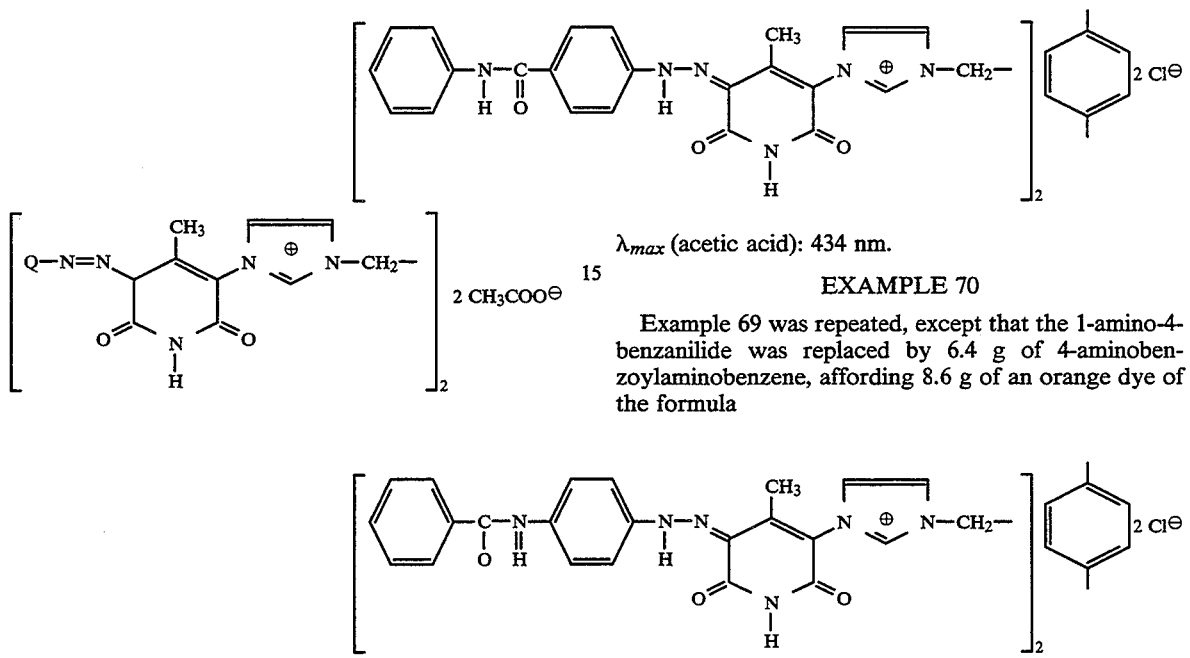

| Example No. | Q | $\lambda_{max}$ [nm] |
|---|---|---|
| 64 | 3,5-dimethylphenyl | 433.1 |
| 65 | 4-(phenylaminocarbonyl)phenyl | 429.1 |
| 66 | 4-(phenylazo)phenyl | 449.1 |
| 67 | 4-methyl-2-oxo-1,2-dihydroquinolin-7-yl | 442.1 |
| 68 | 4-(4-methylbenzoyl)phenyl | 424.1 |

The dyes mentioned in Examples 43 to 68 give brilliant dyeings on bleached pulp with greenish yellow to orange shades.

EXAMPLE 69

6.4 g of 1-amino-4-benzanilide were diazotized as described in Example 40 and coupled to 10.3 g of 1,4-bis[3-(4-methyl-6-hydroxypyrid-2-on-1-yl)-imidazol-1-yliummethyl)]benzene chloride. This produced 11 g of a yellow dye of the formula $\lambda_{max}$ (acetic acid): 434 nm.

EXAMPLE 70

Example 69 was repeated, except that the 1-amino-4-benzanilide was replaced by 6.4 g of 4-aminobenzoylaminobenzene, affording 8.6 g of an orange dye of the formula $\lambda_{max}$ (acetic acid): 456 nm.

EXAMPLE 71 (use)

50 g of wastepaper (wood-containing) were beaten in 1 l of water (10° German hardness) at room temperature to form a fiber suspension. It was diluted with 1 l of the same water. A mixture of 2 g of a 10% strength solution of the dye of Example 1 in acetic acid and 10 ml of water was added. The mixture was gently stirred for 15 minutes and then diluted with water to a solids content of 0.5%. This suspension was used to a produce 80 g/m² sheets of paper on a laboratory sheet former from Franck, and the moist sheets were dried at 100° C. for 5 minutes. This produced a yellow grocery paper. The wastewater was colorless. The bleed fastness of the colored paper (DIN 53 991) was very good, as was the lightfastness.

Similar results were obtained on replacing the wastepaper by a) a mixture of 30% birch sulfate pulp and 70% pine sulfate pulp, by b) pine sulfite pulp and c) pine sulfate pulp. Each variation produced a yellow paper having excellent fastness properties.

EXAMPLE 72 (use)

15 kg of wastepaper (wood-containing), 25 kg of bleached groundwood and 10 kg of unbleached sulfate pulp were beaten in a pulper to a 3% strength aqueous suspension. The suspension was diluted to 2% in a coloring vat. This suspension was then admixed in succession with—calculated on dry total fiber—0.5% of soluble, oxidatively degraded cornstarch, 5% of kaolin and 1.25 kg of a 5% strength acetic acid solution of the dye of Example 13 by stirring. After 20 minutes the stock was admixed in the mixing vat with 1% (based on absolutely dry fiber) of a resin size dispersion. The homogeneous stock suspension was adjusted with alum to pH 5 on the paper machine just upstream of the box.

The paper machine was used to produce an 80 g/m² bag paper which had an orange shade with good bleed fastness properties as defined in DIN 53 991.

EXAMPLE 73 (use)

25 kg of catalog paper (spoils), 60 kg of bleached groundwood (65° Schopper Riegler) and 15 kg of unbleached sulfite pulp were wetted out in a pulper in 2,500 l of water. The 4% strength aqueous suspension was admixed with 0.4% of soluble starch, 16% of kaolin and 2% of talc (calculated on absolutely dry fiber). The suspension was then beaten in a refiner to 45° Schopper Riegler. 40 kg of a 3% strength acetic acid solution of the dye of Example 40 were added (=1% dry dye, based on absolutely dry fiber). After the stock had been allowed to draw for 15 minutes, a resin size dispersion was added (amount: 0.6% dry, based on absolutely dry fiber). After 10 minutes the stock flowing out of the mixing vat was continuously diluted with water to a consistency of 0.8% and continuously adjusted with alum (Al₂(SO₄)₃.18 H₂O) to a pH of 4.5 (measured in the wire water) and pumped into the box.

This produced a golden yellow catalog paper (60 g/m²) having good bleed fastness properties.

We claim:

1. A biscationic azo dye of the formula:

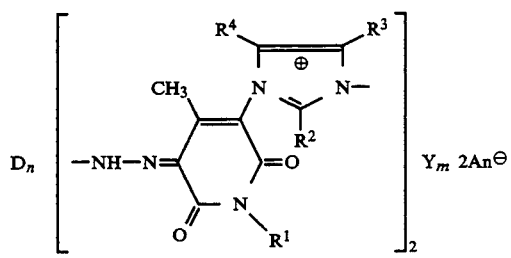

wherein
R¹ is hydrogen or unsubstituted or phenyl-substituted $C_1$–$C_5$-alkyl,
R² is hydrogen or $C_1$–$C_5$-alkyl,
R³ and R⁴ are identical or different and each is independently hydrogen or methyl
D is a radical of a sulfo-devoid aromatic or heteroaromatic diazo component, unsubstituted or $C_1$–$C_4$-alkyl- or $C_1$–$C_4$-alkoxy-substituted 1,4-phenylene or a radical of the formula:

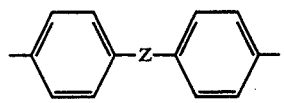

wherein Z is $C_2$–$C_6$-alkylene, $C_2$–$C_6$-alkylenoxy or a radical of the formula —CH=CH—, —NH—CO—, —N=N—, —NH—CO—NH—,

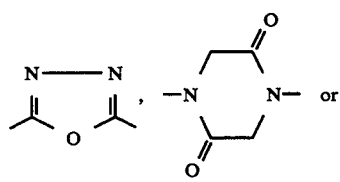

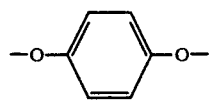

Y is hydrogen, $C_1$–$C_{18}$-alkyl, $C_2$–$C_6$-alkylene, xylidene or phenylene,
An⊖ is an anion
m is 1 or 2, and n is 1 or 2,
with the proviso that
a) in the case of Y being hydrogen or $C_1$–$C_{18}$-alkyl, m is 2, n is 1 and D is unsubstituted or $C_1$–$C_4$-alkyl- or $C_1$–$C_4$-alkoxy-substituted 1,4-phenylene or a radical of the formula

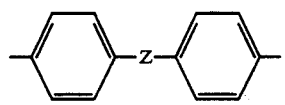

and
b) in the case of Y being $C_2$–$C_6$-alkylene, xylidene or phenylene, m is 1, n is 2 and D is a radical of a sulfo-devoid aromatic or heteroaromatic diazo component.

2. The biscationic azo dye as claimed in claim 1 wherein Y is hydrogen or $C_1$–$C_5$-alkyl,
D is phenylene or a radical of the formula

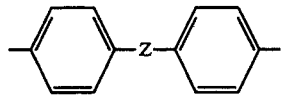

m is 2, and n is 1.

3. The biscationic azo dye as claimed in claim 1, wherein
Y is $C_2$–$C_6$-alkylene, xylidene or phenylene,
D is a radical of a sulfo-devoid aniline diazo component,
m is 1, and
n is 2.

4. A doubled imidazolyl pyridone of the formula

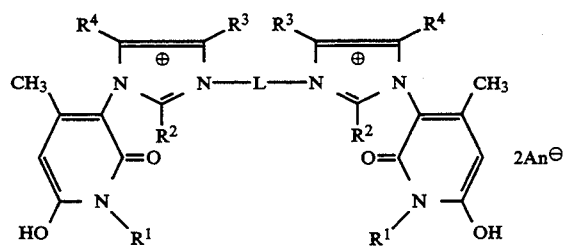

wherein
L is $C_2$–$C_6$-alkylene, xylidene or phenylene,
R¹ is hydrogen or unsubstituted or phenyl-substituted $C_1$–$C_5$-alkyl,
R² is hydrogen or $C_1$–$C_5$-alkyl,
R³ and R⁴ are identical or different and each is independently hydrogen or methyl, and
An⊖ is an anion.

5. A method of dyeing or printing polymeric material comprising immersing said polymeric material in a solution of the biscationic azo dye as claimed in claim 1.

* * * * *